United States Patent
Gobbi Frattini

(10) Patent No.: US 9,988,601 B2
(45) Date of Patent: Jun. 5, 2018

(54) METHOD FOR RETRIEVAL OF STEM CELLS FROM HUMAN AND ANIMAL BLOOD USING AN OXYGEN-OZONE MIXTURE

(71) Applicant: Paolo Gobbi Frattini S.R.L., Milan (IT)

(72) Inventor: Paolo Giuseppe Gobbi Frattini, Sondalo SO (IT)

(73) Assignee: PAOLO GOBBI FRATTINI S.R.L., Milan (IT)

( * ) Notice: Subject to any disclaimer, the term of this patent is extended or adjusted under 35 U.S.C. 154(b) by 51 days.

(21) Appl. No.: 15/027,709

(22) PCT Filed: Oct. 6, 2014

(86) PCT No.: PCT/IB2014/065077
§ 371 (c)(1),
(2) Date: Apr. 7, 2016

(87) PCT Pub. No.: WO2015/052627
PCT Pub. Date: Apr. 16, 2015

(65) Prior Publication Data
US 2016/0251620 A1    Sep. 1, 2016

(30) Foreign Application Priority Data

Oct. 9, 2013 (IT) ................ MI2013A1667

(51) Int. Cl.
*C12N 5/00* (2006.01)
*C12N 5/078* (2010.01)
*G01N 33/50* (2006.01)
*B01D 21/26* (2006.01)

(52) U.S. Cl.
CPC ........... *C12N 5/0634* (2013.01); *B01D 21/26* (2013.01); *G01N 33/5002* (2013.01)

(58) Field of Classification Search
None
See application file for complete search history.

(56) References Cited

U.S. PATENT DOCUMENTS

| | | | | |
|---|---|---|---|---|
| 4,632,980 A * | 12/1986 | Zee | ........................ | A61L 2/0094 424/529 |
| 5,409,825 A * | 4/1995 | Hoffman | .............. | C12N 5/0647 435/384 |
| 5,709,992 A * | 1/1998 | Rubinstein | ............ | A61L 2/0088 435/2 |
| 5,834,030 A * | 11/1998 | Bolton | ................... | A61K 35/14 422/24 |
| 5,980,954 A * | 11/1999 | Bolton | ................... | A61K 33/40 422/24 |
| 6,136,308 A * | 10/2000 | Tremblay | ........... | A61K 41/0004 424/93.7 |
| 6,303,154 B1 | 10/2001 | Breivogel et al. | | |
| 7,045,124 B1 * | 5/2006 | Hamet | ................ | A61M 1/3681 424/93.7 |
| 2003/0108536 A1 * | 6/2003 | Spaner | ................. | C12N 5/0636 424/93.71 |
| 2010/0189807 A1 * | 7/2010 | Werner | ................. | A61K 33/00 424/613 |

FOREIGN PATENT DOCUMENTS

EP    0 607 593 A2    7/1994

OTHER PUBLICATIONS

International Search Report, dated Feb. 2, 2015.
Written Opinion of the International Searching Authority, dated Feb. 2, 2015.
Salma Hasan et al., "Isolation of Human Blood Progenitor and Stem Cells from Peripheral Blood by Magnetic Bead", Bio-Protocol, Nov. 5, 2012 (4 pages).
A. Larini et al., "Effects of ozone on isolated peripheral blood monoculear cells", Toxicology in Vitro, Elseview Science, GB, vol. 19, No. 1, Feb. 1, 2005, pp. 55-61.

* cited by examiner

*Primary Examiner* — Blaine Lankford
(74) *Attorney, Agent, or Firm* — Jacobson Holman, PLLC.

(57) ABSTRACT

The present invention relates to a method for retrieving more numerous, viable and efficient stem cells from the blood of a patient. The method comprises a preliminary step of pre-treating blood cells using an oxygen-ozone mixture and a subsequent step of separating the stem cells from said pre-treated blood cells.

9 Claims, No Drawings

METHOD FOR RETRIEVAL OF STEM CELLS FROM HUMAN AND ANIMAL BLOOD USING AN OXYGEN-OZONE MIXTURE

FIELD OF THE INVENTION

The present invention relates to a method for retrieving active and efficient staminal (stem) cells from human and animal blood.

PRIOR ART

Currently there are several techniques for separating blood cells in order to retrieve a cell population of interest, in particular a stem cell population.

However, most of the known techniques for separating blood cells includes at least one centrifugation step which may become a cause for stress and possible damage to the cells. Such cells thus damaged will be less effective when they are transplanted into the patient.

Therefore, there is a need for implementing a method to obtain the retrieval of stem cells having better "quality" and efficiency and reduce damage due to the process of separating them from blood cells.

Therefore, it is an object of the present invention to provide an efficient method for obtaining stem cells having better quality.

SUMMARY OF THE INVENTION

Therefore, in a first aspect, the present invention relates to a method for retrieving stem cells as defined in claim 1.

The Applicant of the present application has surprisingly found that a very effective method for retrieving stem cells comprises a preliminary step of pre-treating blood cells from patient's blood using an oxygen-ozone mixture before their subsequent use in a step of separating stem cells.

In fact, said preliminary step of pre-treating blood allows a better quality of blood cells and a multiplication thereof to be obtained, in particular of stem cells, regardless of the technique then used for separating the stem cells and in particular following further cryopreservation and thawing steps.

The stem cells from blood pre-treated with said oxygen-ozone mixture before separation are more numerous, viable and active, thus increasing their effectiveness when transplanted into the patient.

Said oxygen-ozone mixture uses adequate amounts and concentrations of such components of the mixture; said oxygen-ozone mixture preferably comprises from about 40% to about 60% by weight of oxygen ($O_2$) and from about 60% to about 40% by weight of ozone ($O_3$), more preferably from about 45% to about 55% by weight of oxygen and from about 55% to about 45% by weight of ozone, with respect to the total weight of the mixture. More preferably, said mixture comprises oxygen and ozone in a ratio of about 1:1 weight/weight.

Preferably, in said oxygen-ozone mixture, the concentration of ozone is from about 20 µg/ml to about 60 µg/ml, more preferably from about 40 µg/ml to about 50 µg/ml.

In fact, on the one hand, when the concentration of ozone in said oxygen-ozone mixture is lower than 20 µg/ml, no effective results are achieved while, on the other hand, when the concentration of ozone in said oxygen-ozone mixture is greater than 60 µg/ml, the practice of major autohemotransfusion, i.e. the collection and re-infusion of a significant amount of blood mixed with a predetermined amount of oxygen-ozone, for example about 200-250 cc, is not allowed.

Once the blood cells have been pre-treated with said oxygen-ozone mixture, they can be separated by means of any cell separation technique.

Such a cell separation step is required to administer to the patient the fraction required to correct the specific problem or cryopreserve only the cell population of interest, in particular stem cells, for example from umbilical cord, bone marrow, peripheral blood or others.

The separation preferably takes place by first producing a biocompatible liquid capable of separating the different cell components of blood (red blood cells, buffy coat and plasma) without the aid of a centrifuge and with separation efficiency in short times. The above-mentioned liquid needs to ensure a clean separation and an isolation of red blood cells from the other cell components of blood. The liquid of interest may be sterilizable by gamma rays and compatible with dimethyl sulfoxide (DMSO). The starting blood is whole blood and the final object is the retrieval of the fraction of white blood cells containing stem cells.

For example:
Liquid Composition:
POLYMER
250 KDa 5% w/w Dextran
500 KDa 15% w/w Dextran
X3.0 BUFFER
0.137 M NaCl
5.4 mM KCl
0.25 mM Na2HPO4
0.44 mM KH2PO4
1.3 mM CaCl2
1.0 mM MgSO4
4.2 mMM NaHCO3
Method The desired dilutions are selected and according thereto the amounts of polymer and buffer to be added to the blood are calculated.

The polymer+buffer mixture is added to the blood bag. The bag is gently stirred to allow an even diffusion of the mixture into the blood.

The bag is hung and left still, so as to allow the solution to act.

With the naked eye it is possible to observe the achievement of separation of the different components of blood (red blood cells, buffy coat and plasma), and the time required to obtain a clean separation is calculated.

| | | | | Ex. | | | |
|---|---|---|---|---|---|---|---|
| BAG NO. | PT UCB | LIQUID | BLOOD (ml) | DILUTION (%) | VOLUME RATIO | POLYMER (ml) | BUFFER (ml) |
| 2 | P D | ST | 70 | 6% | 1:1 | 4.2 | 65.8 |
| 3 | P P | ST | 92 | 6% | 11 | 5.52 | 86.48 |
| 4 | B D | ST | 52 | 6% | 11 | 3.12 | 48.88 |

The following tests are performed on a "baseline" sample (before separation) and on a manipulated sample (after separation).

Hemochrome

Flow cytometer viability

Flow cytometer CD34 expression

Clonogenic assay: for example seeding 45×103 cells on MethoCult GFH8 medium

Alternatively, said step of separating blood cells takes place by means of the centrifugation technique, according to which whole blood is firstly collected from the donor and is then allowed to flow into a centrifugation system which, by accelerating the sedimentation process, allows the cells to be separated from one another and to be separated from plasma.

Centrifugation is a technique which takes advantage of the force generated by a centrifuge and is used in the laboratory to purify macromolecular complexes, micelles, cells and large cell structures, extracellular material, etc., based on their different density with respect to the medium in which they are suspended or dispersed.

The material to be centrifuged is usually placed into tubes accommodated in the rotor of a centrifuge. The rotor is spun at high speed (up to 100,000 revolutions per minute) for a certain time, thus subjecting the suspension to centrifugal forces equal to several thousand times the forces of gravity, which cause the sedimentation of particles that have even slight differences of density with respect to the medium in which they are.

From a certain amount of cell material usually two fractions are separated: the pellet, which is a compact material that remains on the bottom, and the supernatant, which is everything that is left in suspension.

Alternatively, said step of separating blood cells preferably takes place by means of the filtration technique, according to which whole blood collected from the donor is allowed to flow in a filtering module of microporous membranes which allow the separation of plasma protein molecules from cells, which cannot cross such membranes.

Yet, in a further alternative, said step of separating blood cells takes place by means of the combination of the above-mentioned filtration and centrifugation techniques, where the blood flows into a cylinder containing a membrane preferably made of polycarbonate with small sized pores (a few microns). Centrifugation allows the various constituents of blood to be separated and rotation sends the cells away from the membrane, thus preventing the saturation of the filter. The solution containing the cells is then allowed to flow in a reservoir, while the plasma (containing or not platelets, depending on the procedure) goes into a collection bag.

Further features and advantages of the present finding will become more apparent from the consideration of the following detailed description of a preferred but non-exclusive embodiment, illustrated by way of non-limiting example.

DETAILED DESCRIPTION

The following detailed description relates to a particular embodiment of the invention, which has confirmed the validity and advantages of the claimed method.

By using a syringe, a predetermined amount of oxygen-ozone mixture at the concentration of interest is collected and added to a bag containing the blood to be subjected to the cell separation step. Afterwards, the cell separation procedure is performed.

Example 1 (Invention)

An oxygen-ozone mixture with a 1:1 oxygen-ozone ratio and a concentration of ozone of about 40 µg/ml was collected; such a mixture was added to a bag containing blood; therefore, the bag was stirred for a few seconds to allow the oxygen-ozone mixture to distribute evenly throughout the blood inside the bag.

A certain amount of the pre-treated blood with such an oxygen-ozone mixture was then firstly collected from such a bag with a syringe conditioned with heparin, citrate or other anticoagulant to prevent the blood itself from clotting and, then, transferred from the syringe to a container, pressing the plunger very slowly to prevent the cells from breaking.

In another container, about half of the volume—with respect to the blood—of Histopaque® 1077 (available from Sigma-Aldrich, St. Louis, Mo., USA), a non-sterile solution based on polysucrose and sodium diatrizoate corrected to a density of 1.077±0.001 g/ml, was placed at room temperature. In the container containing Histopaque® 1077 a volume of blood diluted with saline was added very slowly, so that the two solutions remained separate. The mixture obtained was centrifuged at 1500 rpm for 30 minutes at 25° C., obtaining 4 distinct phases: red blood cells underneath, Histopaque® 1077 slightly above, then a thin ring of mononuclear cells and plasma on top.

With the aid of a suction blower the cell ring was drawn, transferred to a container and taken to 50 ml with saline. Afterwards it was resuspended, centrifuged at 1500 rpm for 15 minutes at 25° C.; this operation was repeated several times until all the supernatant was eliminated.

The cells thus separated were washed and stored at a temperature of −4° C.

Alternatively, the above-described biocompatible liquid could have been used instead of centrifugation with particularly advantageous effects.

Example 2 (Comparison)

A blood bag similar to that used in Example 1 was taken, except that such a bag was not subjected to the pre-treatment step with the addition of the oxygen-ozone solution.

The cells contained in such a bag were subjected to the same separation step as described in Example 1.

Evaluation Test

Bag 1 containing cells obtained by means of the pre-treatment of the invention described in Example 1 and bag 2 containing cells obtained as described in Comparative Example 2 (without such a pre-treatment) were assessed by means of a standard evaluation test.

The standard evaluation tests are usually based on the analysis of cell viability and the count of CD34+ cells (antigenic marker common to hematopoietic progenitors which may be recognized by monoclonal antibodies) which could participate in the formation, auto-reproduction and differentiation of stem cells.

The cell viability of cells adhered or in suspension contained in the above-described bag 1 and bag 2 was assessed with flow cytometry techniques, by using 7-Aminoactinomycin, for example, or contacting the cells with a solution of Trypan Blue dye (0.4%) (available for example from Sigma-Aldrich as T-8154) for 5 minutes. Following such a treatment, live cells did not take the dye and appeared refracting, while dead cells appeared blue-stained since they lost their capability of excluding the dye.

The CD34+ cell count was assessed by means of flow cytometry, for example with 7-Aminoactinomycin, which technology allows a great number of cells to be analyzed in a short time (50,000 cells in a few seconds) and several parameters to be quantified for each single cell based on the information provided by a light beam which crosses each single cell and determines the emission of a fluorescence signal therefrom.

The cells of bag 1 which were subjected to the pre-treatment of the present invention showed a considerable increase in the number of viable CD34+ with respect to those of bag 2 not subjected to such a pre-treatment.

Moreover, the cells of bag 1 and bag 2 were also subjected to a proliferation assay, that is an assay used to confirm any effect on the proliferation rate due to damage or death of cells. Such an assay provides for the cells in exponential growth to be seeded in plates and incubated in standard culture conditions; non-treated cells and cells treated with solvent alone are used as the negative controls.

Following such a proliferation assay, the cells of bag 1 which were subjected to the pre-treatment of the present invention also showed improved state and enhanced quality of the same cells (stem cells proliferated well) and the presence of stem cell markers, such as for example for hematopoietic stem cells CD14, CD34 and CD45, with respect to those of bag 2 not subjected to such a pre-treatment.

Therefore, the stem cells from whole blood pre-treated with oxygen-ozone mixture before separation, according to the method of the present invention, were more numerous, viable and active. Therefore, their effectiveness was increased when they were transplanted into the patient.

It should be noted that in application EP 0 607 593 A2 a method that includes the "fumigation" of cell cultures of various origin (whole blood, leukocytes, lymphocytes, urine) with a gas mixture of oxygen-ozone for the production of cytokines, which are cell messengers produced by the cells that play several roles of "communication" among the cells themselves, had already been described. The above-mentioned application states that the oxygen-ozone mixture is capable of activating the metabolism of cells and thus of increasing the production of cytokines. It is claimed that the therapeutic use of cytokines produced with such a method in malignant tumors is better than the use of stem cells.

In application EP 0 607 593 A2 no reference is made to the treatment of blood cells with oxygen-ozone in order to retrieve more numerous, active and viable stem cells.

The invention claimed is:

1. A method for retrieving stem cells from the blood of a patient, the method comprising a preliminary step of pre-treating the blood cells by an oxygen-ozone mixture and a subsequent step of separating the stem cells from said blood cells, wherein said preliminary step comprises the succession of preparing an oxygen-ozone mixture, collecting a predetermined amount of said oxygen-ozone mixture by means of a syringe, adding said predetermined amount of oxygen-ozone mixture to a blood containing bag and stirring the bag to allow the oxygen-ozone mixture to distribute evenly throughout the blood inside the bag wherein said oxygen-ozone mixture comprises about 40% to about 60% by weight of oxygen and from about 60% to about 40% by weight of ozone, with respect to the total weight of the mixture.

2. The method according to claim 1, wherein said oxygen-ozone mixture comprises from about 45% to about 55% by weight of oxygen and from about 55% to about 45% by weight of ozone, with respect to the total weight of the mixture.

3. The method according to claim 1, wherein said oxygen-ozone mixture comprises oxygen and ozone in a ratio of about 1:1 weight/weight.

4. The method according to claim 1 wherein in said oxygen-ozone mixture the concentration of ozone is from about 20 µg/ml to about 60 µg/ml.

5. The method according to claim 4, wherein the concentration of ozone is from about 40 µg/ml to about 50 µg/ml.

6. The method according to claim 1, wherein the step of separating the stem cells, following said preliminary pre-treatment step, takes place by means of any technique for separating blood cells.

7. The method according to claim 6, wherein said method for separating blood cells takes place by using a biocompatible liquid capable of separating the different cell components of blood without the aid of a centrifuge and with separation efficiency in short times.

8. The method according to claim 7, wherein said biocompatible liquid is sterilizable by gamma rays and compatible with dimethyl sulfoxide.

9. The method according to claim 6, wherein said separation of stem cells takes place by centrifugation.

* * * * *